(12) United States Patent
Bognar

(10) Patent No.: US 12,274,853 B2
(45) Date of Patent: Apr. 15, 2025

(54) PICC LINE SEPARATOR

(71) Applicant: Atilla Kennedy Bognar, Los Angeles, CA (US)

(72) Inventor: Atilla Kennedy Bognar, Los Angeles, CA (US)

(*) Notice: Subject to any disclaimer, the term of this patent is extended or adjusted under 35 U.S.C. 154(b) by 0 days.

(21) Appl. No.: 17/110,213

(22) Filed: Dec. 2, 2020

(65) Prior Publication Data
US 2023/0075683 A1    Mar. 9, 2023

(51) Int. Cl.
*A61M 39/16* (2006.01)
*A61B 90/70* (2016.01)

(52) U.S. Cl.
CPC ............ *A61M 39/16* (2013.01); *A61B 90/70* (2016.02)

(58) Field of Classification Search
CPC ............................. A61M 39/16; A61B 90/70
See application file for complete search history.

(56) References Cited

U.S. PATENT DOCUMENTS 4,296,949 A * 10/1981 Muetterties ............ A61M 39/10
                                                     285/332
2020/0246593 A1* 8/2020 Chiang ............... A61M 39/1011

* cited by examiner

*Primary Examiner* — Bradley J Osinski
(74) *Attorney, Agent, or Firm* — Chang & Hale LLP

(57) ABSTRACT

The present invention relates to a system consisting of one or more instruments, which provides a simple method for detaching a connector cap from the connector as this is the juncture utilized to administer fluids into the body via an IV peripherally inserted central catheter, commonly know as a PICC or PIC line. This device enables one to avoid potential breakage of the PICC line connector cap, which can occur utilizing current procedures. The system is put into place whereby the portion of the instrument associated with the fixed end of the PICC line (that which is implanted in the patient) is slid over the PICC line connector and held stationary, while the portion of the accompanying instrument associated with the free end of the PICC line is secured around the connector cap and rotated counterclockwise until the connector cap assembly is loose enough to be separated without further aid.

18 Claims, 4 Drawing Sheets

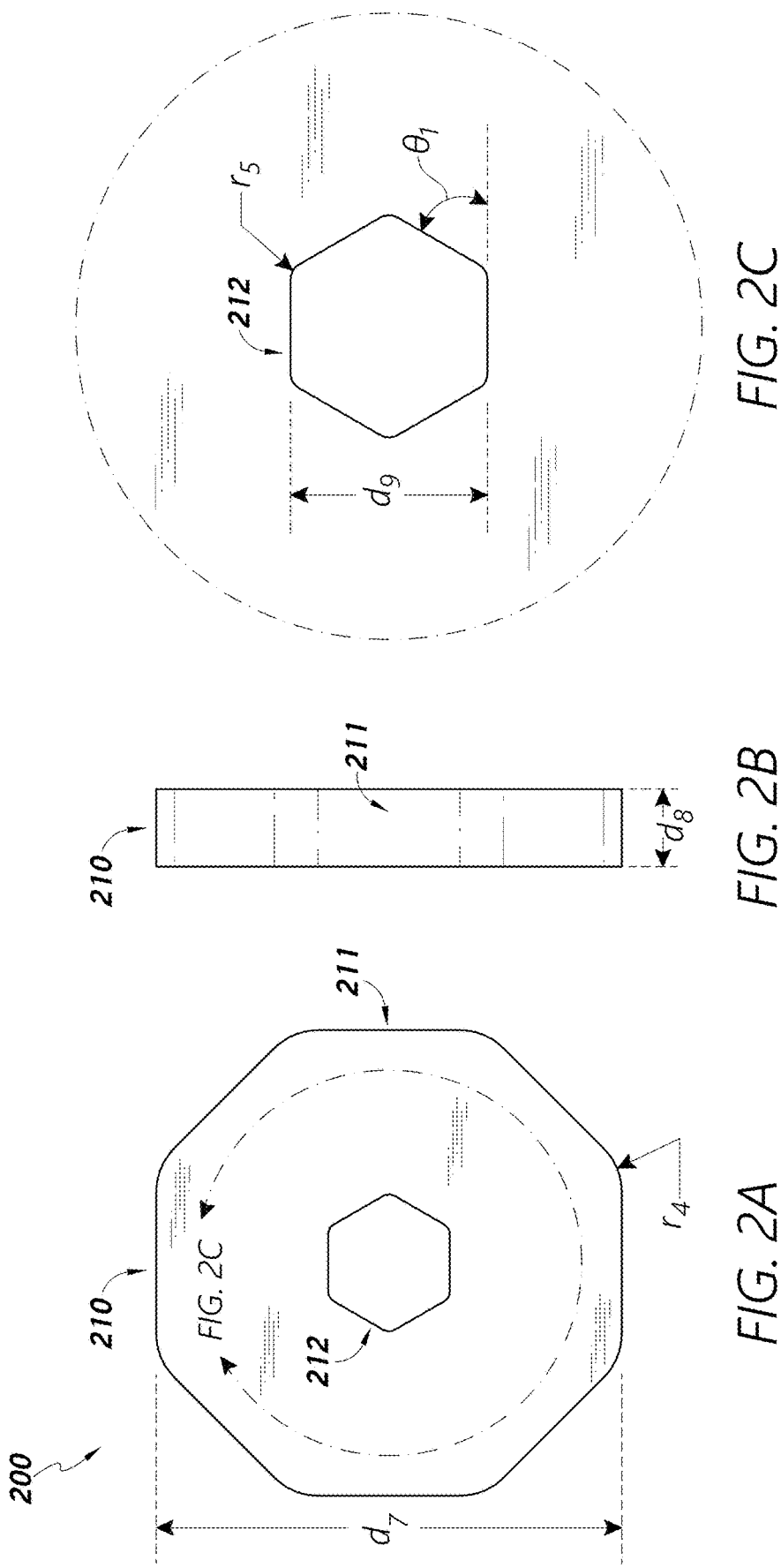

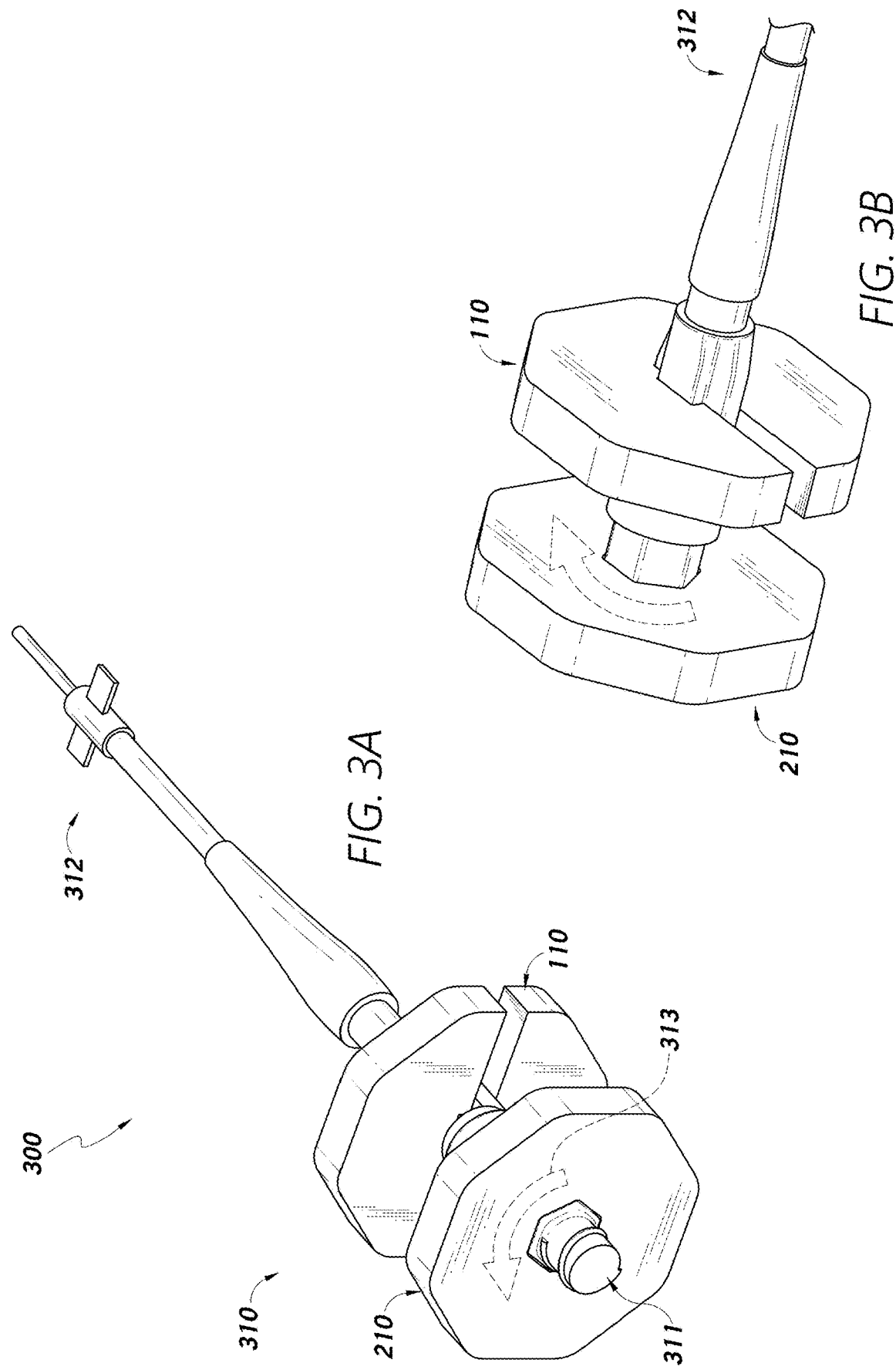

PICC LINE SEPARATOR

BRIEF SUMMARY OF THE INVENTION

The inventive subject matter provides for a solution to potential problems that can arise during the cleaning and replacement of an IV PICC line dressing, often prescribed weekly, to ensure the simple and safe removal of a PICC (also known as PIC) line connector's cap from its connector.

The current removal procedure is twist of the cap. However, problems frequently occur when the cap becomes firmly stuck to the connector and the current solution's utilization of a metal hemostat plier to aid in release can crack the PICC line connector causing, in the best case, the pain and expense of inserting a new PICC line into the patient.

The present invention provides a method that enables one to avoid potential connector breakage by replacing the crushing force of a metal hemostat plier onto delicate plastic parts with the gentle torsional force of a custom instrument made of similar hardness plastic dimensionally matching the connector and cap.

DETAILED DESCRIPTION OF THE INVENTION

1. Background

Intravenous therapy (abbreviated as IV therapy) is a medical technique that delivers a liquid directly into a person's vein, especially when rapid distribution is desired. The intravenous route of administration is commonly used for rehydration solutions or to provide nutrition in those who cannot consume food or water by mouth. It may also be used to administer medications or other medical therapy such as blood products or electrolytes to correct electrolyte imbalances.

A common type of IV therapy is the peripherally inserted central catheter (PICC or PIC line), less commonly called a percutaneous indwelling central catheter, which is a form of intravenous access that can be used for a prolonged period of time (e.g., for long chemotherapy regimens, extended antibiotic therapy, or total parenteral nutrition) or for administration of substances that should not be done peripherally (e.g., antihypotensive agents a.k.a. pressors). It is a catheter that enters the body through the skin (percutaneously) at a peripheral site, extends to the superior vena cava (a central venous trunk), and stays in place (dwells within the veins) for days or weeks.

Generally, PICC lines are considered when a person is expected to need more than two weeks of intravenous therapy. A PICC line can remain inserted for an extended period of time compared to other forms of central IV access, ranging from seven days up to several months as long as the line remains viable. They are utilized in both the hospital and community settings. They are commonly used in people receiving total parenteral nutrition (TPN), chemotherapy, or long-term medications such as antibiotics.

To help prevent infections or the line from becoming clogged, PICC line dressings should be changed, and the area and connector should be regularly flushed with normal saline, and "locked" by filling it with Heparin or normal saline when not in use and the cap covering the connector is replaced.

The PICC Line Separator was invented by Atilla Bognar, a concerned father, in response to multiple problems experienced by his young daughter during the changing of her PICC line dressing in hospital settings. These resulted in the need for repeated replacement of her PICC line which, as noted by the Mayo Clinic, can increase the risk of vascular damage. He recounts his daughter's experiences, the problem and his solution:

"My daughter is a 14 yr. old child being treated at a highly regarded Children's hospital in Southern California. She has a 'PICC' line in her arm for an intravenous feeding bag that holds a large amount of vitamin infused liquid mixture that is sent directly to a heart vein for 10 hours at night. This method ensures nutrients as her body does not break down foods thoroughly, as is the case for many people with IBD, irritable Bowel Syndrome. A weekly dressing change is needed whereupon the PICC line connector's cap gets separated from the connector and gets replaced for cleanliness to ensure that the tube and end connector remain clean flowing. The 'cap' gets replaced; the connector remains in place.

I do the dressing changes at home now because the infusion center at the hospital broke her 'PICC' connector last year during a dressing change by using two metal clamps (hemostats) to twist the cap off. This was done by the lead CVC (central venous catheter) team nurse. A hairline crack in the connector (which remains in-place) caused blood to feed backwards and spray blood everywhere after arriving home and she woke up in a pool of blood. I rushed back to the Emergency room where I was informed my daughter would have to undergo the surgical replacement of a new PICC line.

A year later, a nurse did the same thing, again crushing the plastic connector trying to remove a stuck cap with metal tools. This second time was while she was in the hospital sleeping, and awoke to blood spraying out of her arm. The attending nurse didn't know what to do (I was later told she could have bled out!). Another nurse came over, clamped her line and shut off the pump, and prepared my daughter for the procedure to insert a new PICC line. My daughter now had three scars on her arm, when there should only be one.

This 3rd surgical procedure caused considerable, and unnecessary, suffering for my daughter. She became terrified that it would happen again and I felt I had to do something. I convinced the hospital to train and certify me to replace the dressings at home where I initiated a procedure to immobilize the connector allowing the connector cap to be removed without the risk of crushing the connector, and from this concept I developed a tool to both eliminate the problem of crushed connectors and create a simple standard procedure for the connector cap decoupling process. Having your child 'put under' for a one time PICC line insertion procedure is stressful enough, it shouldn't happen repeatedly because of a poor excuse such as 'the line just broke'."

2. How it is Used

The system is put into place during the PICC line dressing's clean and change procedure which may typically occur weekly, whereby the instrument portion associated with the fixed end of the PICC line (that which is implanted in the patient) is slid over the PICC line and onto the connector and held stationary, while the portion of the instrument associated with the free end of the PICC line, is secured around the connector cap and rotated counterclockwise until the connector cap assembly is loose enough to be separated without further aid of a tool.

3. How it Differs from the Current Method

The current method of separating PICC line interfaces is to twist the cap off by hand, however problems may occur when the cap becomes firmly stuck to the connector. The current solution requires improvisation by using a metal hemostat plier and tourniquet strap. The tourniquet strap is used in an attempt to cushion the soft plastic PICC line components from the hard metal surfaces and crushing forces of the hemostat plier. This method is highly variable and dependent on the user regulating the force applied. It has often resulted in the connector being broken with no other option than an expensive and uncomfortable surgical procedure to replace it. The new method uses an instrument, which may be made of plastic material of a similar hardness as the PIC connector and cap with a safety benefit of a superior composite strength, thereby reducing fully the unsafe practice of using a metal tool on a plastic part. It should also be noted that the crushing force of the current improvised method actually makes separation more difficult as the outer shell is squeezed against the inner mating part of cap/connector assembly. Additionally, since the instrument(s) in the PICC Line Separator has no moving parts it cannot crush the delicate components. In fact, as the working faces of the instrument(s) are custom designed to mate perfectly with and use the strongest areas of the PICC line connector and cap, only torsional forces are applied and the risk of catastrophic damage is minimized while separation of stuck interfaces is greatly aided. Use of the PICC Line Separator results in an extremely repeatable and consistent process that is much less dependent upon user input and susceptible to such variations.

4. How It's Made

The PICC line Separator may be manufactured utilizing CNC milling of acetal homopolymer (Delrin®) sheets of appropriate thickness. This method may be satisfactory for small batch production runs. For higher volume manufacturing, injection molding may be the most practical. Finally, any manufacturing technique capable of holding the required tolerance of +/−0.002" in acetal homopolymer may be acceptable.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

With regard to FIGS. 1A, 1B, and 1C, the PICC line connector manipulator piece/disk/instrument/tool 110 can have any of the following example dimensions. The piece 110 can have a diameter $d_1$ in the range of 1.5"±0.005". The piece 110 can have a thickness $d_2$ in the range of 0.25"±0.005". The piece 110 can have an octagonal outer circumference with at least partially straight sides, with rounded corners between adjacent ones of the sides, the rounded corners having a radius of curvature in the range of 0.2"±0.005".

The piece 110 can include a straight radial through slot 112 that extends from the outer circumference of the piece on one side and terminates just beyond the central axis/point of the piece 110. At the center of the piece, the slot 112 intersects with a shorter perpendicular internal slot/void/cut-out/bore 114, creating a cross-shaped aperture/void/cut-out/bore. The radial slot 112 may have a width $d_3$ in the range of 0.135"±0.002". A portion 113 of the radial slot 112 may extend beyond the transverse slot 114, such as by a distance $d_5$ in the range of 0.1"±0.002", wherein the extended portion 113 may have a width equal to that of the longer slot arm 112 (e.g., 0.135"±0.002"). The transverse internal slot 114 may have a width do of 0.25"±0.002". Shoulder portions of the transverse internal slot 114 that extend beyond the width of the slot 112 can have a dimension $d_4$ of 0.065"±0.002". The transverse internal slot 114 can have corners with a radius of curvature $r_3$ of ≤0.032". The internal corners at the junctions of the radial slot 112 and the transverse slot 114 can have a radius of curvature $r_2$ of ≤0.032"

With regard to FIGS. 2A, 2B, and 2C, the PICC line connector cap manipulator piece/disk/instrument/tool 210 can have any of the following example dimensions. The piece 210 can have a diameter $d_7$ of 1.5"±0.005". The piece 210 can have a thickness $d_8$ of 0.25"±0.005". The piece 210 can have an octagonal outer circumference with at least partially straight sides, with rounded corners between adjacent ones of the sides, the rounded corners having a radius of curvature $r_4$ of 0.2"±0.005".

The piece 210 can have a hexagonal inner aperture/void/cut-out/bore 212 with at least partially straight sides, with corners between adjacent ones of the sides having a radius of curvature in the range of 0.0322"±0.005". Adjacent hexagonal sides of the aperture 212 can be angled relative to one another by an angle $\theta_1$ of 60°. The aperture 212 can have a diameter $d_9$ in the range of 0.39"±0.002".

REFERENCES CITED

Intravenous Therapy
https://en.wikipedia.org/wiki/Intravenous_therapy
Peripherally inserted central catheter
https://en.wikipedia.org/wiki/Peripherally_inserted_central_catheter#:~:text=A %20peripherally%20inserted%20central%20 catheter%20%28PICC%20or%20PIC,be%20done% 20peripherally%20%28e.g.%2C%20antihypotensive %20agents%20a.k.a.%20pressors%29
https://www.mayoclinic.org/tests-procedures/picc-line/about/pac-20468748

BRIEF DESCRIPTIONS OF THE DRAWINGS

FIGS. 1A, 1B, and 1C show plan, side, and central detailed views, respectively, of a piece of an example PICC Line Separator part comprised of two pieces, this one (110) for holding the PICC line connector in place. Indicated internal dimensions detailed in FIG. 1C (112, 113, 114) are designed to securely hold the PICC line connectors.

FIGS. 2A, 2B, and 2C show plan, side, and central detailed views, respectively, of a piece of an example PICC Line Separator part, comprising two pieces, this one (210) for holding the disposable PICC connector cap, and enabling the operator to apply the proper torque to loosen the cap from the connector, without crushing it. Indicated internal dimensions detailed in FIG. 2C (212) are designed to securely hold the PICC line connector cap.

FIGS. 3A and 3B show perspective views of a 2-piece example PICC Line Separator utilized on a PICC line connector and connector cap. The component (110) has been slipped over the PICC line to hold its connector steady, subsequently the component (210) has been slipped around the connector cap (311) and is rotated counterclockwise (313) to loosen it.

Figures 1A, 1B, 1C:
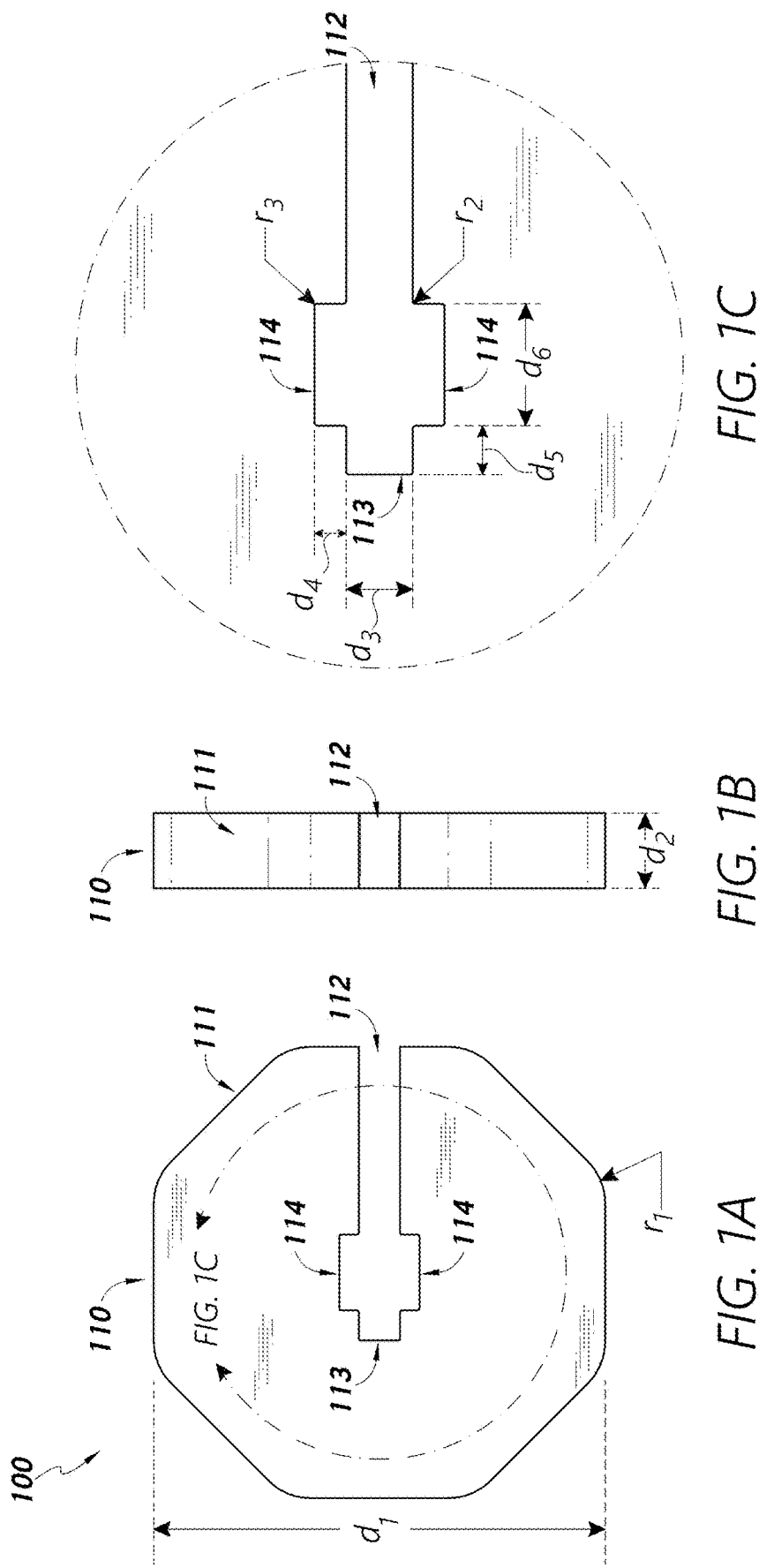
Figure 4:
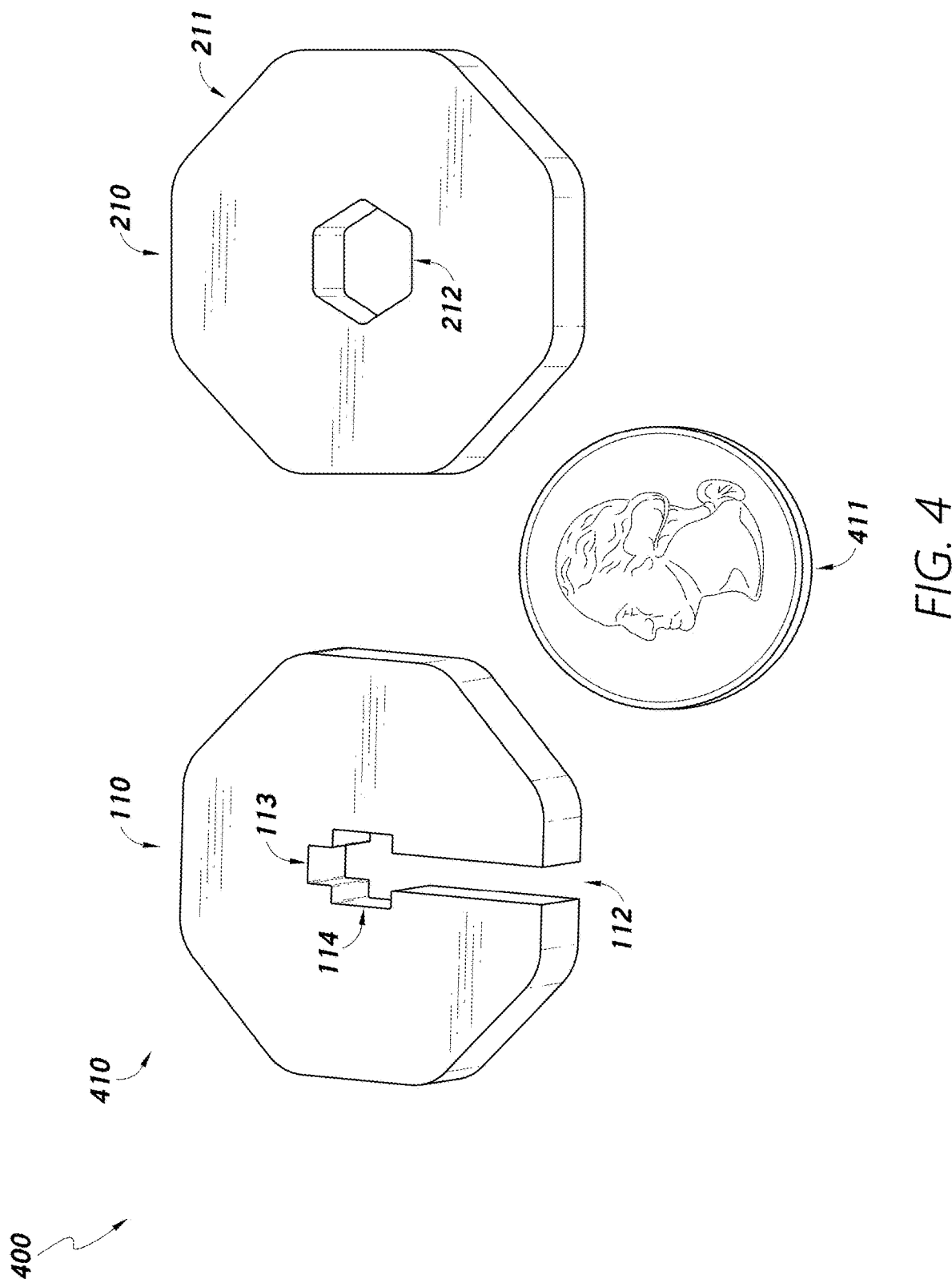
FIG. 4 shows a perspective view of the components (110 and 210) which comprise the 2-piece PICC Line Separator and a US quarter (411), providing a visual reference of size.

What is claimed:

1. A PICC line connector cap manipulator system comprising:
   a first disk comprising:
      a first plurality of straight radial sides; and
      a central hexagonal bore; and
   a second disk comprising:
      a second plurality of straight radial sides;
      a radial slot that extends from one of the second plurality of straight radial sides through a center of the second disk; and
      an internal transverse slot that intersects the radial slot at the center of the second disk to form a cross-shaped central bore;
   wherein the first disk and the second disk have a common thickness.

2. The PICC line connector cap manipulator system of claim 1, wherein:
   the radial slot of the second disk has a width of between 0.133-0.137 inches; and
   the internal transverse slot of the second disk has a width of between 0.248-0.252 inches.

3. The PICC line connector cap manipulator system of claim 1, wherein the first disk and the second disk both have a thickness of between 0.245-0.255 inches.

4. The PICC line connector cap manipulator system of claim 1, wherein the first disk and the second disk have a common profile shape.

5. The PICC line connector cap manipulator system of claim 1, wherein the first disk and the second disk have a octagonal perimeter shape.

6. The PICC line connector cap manipulator system of claim 5, wherein the octagonal perimeter shape has rounded corners between adjacent straight radial sides thereof.

7. The PICC line connector cap manipulator system of claim 1, wherein the internal transverse slot has a width that is greater than a width of the radial slot.

8. The PICC line connector cap manipulator system of claim 1, wherein the first disk and the second disk both comprise acetal homopolymer.

9. The PICC line connector cap manipulator system of claim 1, wherein the radial slot extends beyond the internal transverse slot by a distance of between 0.098-0.102 inches.

10. A method of loosening a PICC line connector cap, the method comprising:
    placing a central hexagonal bore of a first disk instrument over a PICC line connector cap coupled to a PICC line connector;
    sliding a radial slot of a second disk instrument over the PICC line connector; and
    while holding the PICC line connector stationary with the second disk instrument, rotating the first disk instrument counterclockwise, thereby causing counterclockwise rotation of the PICC line connector cap relative to the PICC line connector;
    wherein the first disk instrument and the second disk instrument have a common thickness.

11. The method of claim 10, wherein the common thickness of the first disk instrument and the second disk instrument is less than $1/4$ of a minimum diameter of the first disk instrument and the second disk instrument.

12. The method of claim 11, wherein the common thickness of the first disk instrument and the second disk instrument is approximately $1/6$ of the minimum diameter of the first disk instrument and the second disk instrument.

13. The method of claim 10, wherein the second disk instrument includes a transverse slot that intersects the radial slot to form a cross-shaped central bore.

14. The method of claim 13, further comprising, after said sliding the radial slot of the second disk instrument over the PICC line connector, axially sliding the cross-shaped central bore of the second disk instrument over a cross-shaped form of the PICC line connector.

15. The method of claim 13, wherein the transverse slot has a width that is greater than a width of the radial slot.

16. The method of claim 15, wherein:
    the radial slot has a width of between 0.133-0.137 inches; and
    the transverse slot has a width of between 0.248-0.252 inches.

17. The method of claim 10, wherein the first disk instrument and the second disk instrument both have a thickness of between 0.245-0.255 inches.

18. A PICC line connector cap manipulator system comprising:
    a first disk comprising:
       a first plurality of straight radial sides; and
       a central hexagonal bore; and
    a second disk comprising:
       a second plurality of straight radial sides;
       a radial slot that extends from one of the second plurality of straight radial sides through a center of the second disk; and
       an internal transverse slot that intersects the radial slot at the center of the second disk to form a cross-shaped central bore; and
    wherein:
       the radial slot of the second disk has a width of between 0.133-0.137 inches; and
       the internal traverse slot of the second disk has a width of between 0.248-0.252 inches and a length between 0.248-0.252 inches.

* * * * *